US012594081B2

(12) United States Patent
Lark et al.

(10) Patent No.: US 12,594,081 B2
(45) Date of Patent: Apr. 7, 2026

(54) MEDICAL CUTTING DEVICES WITH STATIC COMPONENTS HAVING TEMPERATURE SENSORS AND RELATED METHODS

(71) Applicant: Innovations 4 Surgery, LLC, Chapel Hill, NC (US)

(72) Inventors: Robert K. Lark, Chapel Hill, NC (US); Edward C. Skolnick, Denville, NJ (US); Antoine R. Kaeslin, Bethel, CT (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 490 days.

(21) Appl. No.: 18/087,727

(22) Filed: Dec. 22, 2022

(65) Prior Publication Data

US 2023/0190302 A1     Jun. 22, 2023

Related U.S. Application Data

(60) Provisional application No. 63/292,438, filed on Dec. 22, 2021.

(51) Int. Cl.
| | |
|---|---|
| *A61B 17/14* | (2006.01) |
| *A61B 17/32* | (2006.01) |
| *A61B 17/00* | (2006.01) |
| *A61B 17/56* | (2006.01) |

(52) U.S. Cl.
CPC ...... *A61B 17/142* (2016.11); *A61B 17/32002* (2013.01); *A61B 17/320068* (2013.01); *A61B 2017/00101* (2013.01); *A61B 2017/00115* (2013.01); *A61B 2017/00123* (2013.01); *A61B 2017/320075* (2017.08); *A61B 2017/564* (2013.01); *A61B 2217/007* (2013.01)

(58) Field of Classification Search
CPC ................... A61B 17/14; A61B 17/16; A61B 2017/320075; A61B 17/142; A61B 17/32002; A61B 17/320068; A61B 2017/00084; A61B 2017/00101
See application file for complete search history.

(56) References Cited

U.S. PATENT DOCUMENTS

| | | |
|---|---|---|
| 4,008,720 A | 2/1977 | Brinckmann et al. |
| 5,087,261 A | 2/1992 | Ryd et al. |
| 5,122,142 A | 6/1992 | Pascaloff |
| 5,188,102 A | 2/1993 | Idemoto et al. |
| 5,261,922 A | 11/1993 | Hood |
| 5,728,130 A | 3/1998 | Ishikawa |
| 6,379,371 B1 | 4/2002 | Novak |
| 6,443,969 B1 | 9/2002 | Novak |
| 8,343,178 B2 | 1/2013 | Novak |

(Continued)

*Primary Examiner* — Samuel S Hanna
(74) *Attorney, Agent, or Firm* — Olive Law Group, PLLC

(57) ABSTRACT

Medical cutting devices with static components having temperature sensors and related methods are disclosed. According to an aspect, a cutting device includes a blade working body being configured for operable connection to a source of movement. The cutting device also includes a static component being configured for operable connection to the source of movement. Further, the cutting device includes one or more temperature sensors attached to the static components and configure to detect a temperature level of a work space near the blade working body.

9 Claims, 17 Drawing Sheets

(56) References Cited

U.S. PATENT DOCUMENTS

| | | | |
|---|---|---|---|
| 8,348,880 B2 | 1/2013 | Messerly et al. | |
| D680,218 S | 4/2013 | Darian | |
| 9,320,528 B2 | 4/2016 | Voic | |
| 9,554,809 B2 | 1/2017 | Lark | |
| 10,238,415 B2 | 3/2019 | Naono | |
| 10,702,296 B2 | 7/2020 | Boudreaux | |
| 2003/0204199 A1 | 10/2003 | Novak | |
| 2005/0222598 A1* | 10/2005 | Ho ..................... | A61B 17/3201 |
| | | | 606/171 |
| 2005/0273127 A1 | 12/2005 | Novak | |
| 2008/0009848 A1 | 1/2008 | Paraschiv | |
| 2008/0027449 A1* | 1/2008 | Gundlapalli ....... | A61B 17/1624 |
| | | | 606/82 |
| 2008/0119860 A1* | 5/2008 | McCarthy .............. | A61B 17/15 |
| | | | 606/82 |
| 2013/0204285 A1 | 8/2013 | Gouery | |
| 2015/0005771 A1 | 1/2015 | Voic | |
| 2015/0088137 A1 | 3/2015 | Manna | |
| 2016/0089155 A1 | 3/2016 | Lark | |
| 2017/0056052 A1 | 3/2017 | Dickerson | |
| 2017/0340339 A1 | 11/2017 | Madan | |
| 2017/0340344 A1 | 11/2017 | Boudreaux | |
| 2017/0340345 A1 | 11/2017 | Yates | |
| 2018/0344346 A1 | 12/2018 | Naono | |
| 2019/0142453 A1* | 5/2019 | Efremkin ....... | A61B 17/320068 |
| | | | 606/7 |
| 2021/0121195 A1 | 4/2021 | Richards | |
| 2021/0186525 A1 | 6/2021 | Lark | |

* cited by examiner

MEDICAL CUTTING DEVICES WITH STATIC COMPONENTS HAVING TEMPERATURE SENSORS AND RELATED METHODS

CROSS REFERENCE TO RELATED APPLICATIONS

This application claims priority to U.S. Provisional Patent Application No. 63/292,438, filed Dec. 22, 2021, and titled MEDICAL DEVICES AND RELATED METHODS FOR TRANSFORMING BONE, OTHER TISSUE, OR MATERIAL, the content of which is incorporated herein by reference in its entirety.

This application is related to U.S. Nonprovisional patent application Ser. No. 18/087,715, filed Dec. 22, 2022, and titled MEDICAL CUTTING DEVICES WITH A STATIC CASING AND A BLADE WORKING BODY OF GREATER WIDTH AND RELATED METHODS.

This application is related to U.S. Nonprovisional patent application Ser. No. 18/087,741, filed Dec. 22, 2022, and titled MEDICAL CUTTING DEVICES WITH COOLANT MODULES AND CHANNELS AND ASSOCIATED METHODS.

This application is related to U.S. Nonprovisional patent application Ser. No. 18/087,749, filed Dec. 22, 2022, and titled MEDICAL CUTTING DEVICES HAVING A BLADE WORKING BODY THAT DEFINES AN OPENING FOR EMITTING COOLANT THEREFROM AND RELATED METHODS.

This application is related to U.S. Nonprovisional patent application Ser. No. 18/087,766, filed Dec. 22, 2022, and titled MEDICAL CUTTING DEVICES HAVING A WORKING BLADE BODY WITH STATIC COMPONENTS AND RELATED METHODS OF USE.

TECHNICAL FIELD

The presently disclosed subject matter relates generally to medical devices. Particularly, the presently disclosed subject matter relates to medical cutting devices with static components having temperature sensors and related methods.

BACKGROUND

Traditional surgical saws, such as oscillating saws and reciprocating saws, allow users to cut bones (i.e. perform osteotomies) of relatively large diameters, such as the tibia and femur. These types of surgical saws, however, which are similar in many ways to the toothed saws used to cut wood, metal, and plastic, have significant disadvantages with respect to a patient's well-being. Because surgical saws utilize rapid motion of the saw blade to cut biological tissues, such as bone and cartilage, a significant amount of heat is generated along the blade and particularly at the blade and bone interface. This can be harmful to the patient since prolonged exposure of bone cells to temperatures at or in excess of 47° C. leads to necrosis of those osteocytes. Another disadvantage of these oscillating and reciprocating bone saws is that they produce uneven cuts, preventing ideal realignment and reduction of the osteotomy gap, which is detrimental to efficient healing of the bone. Oscillating bone saws, which utilize a number of sharpened teeth along their cutting edges, can tear neighboring soft tissues that are inadvertently caught in the serrations of the rapidly moving blade. Tearing of these soft tissues leads to significant blood loss and potential nerve damage, which undoubtedly hampers the health of the patient.

Traditional oscillating and reciprocating bone saws have employed a variety of different measures to address these disadvantages. With respect to the generation of excessive heat, these surgical saws can utilize irrigation systems to flush the surgical site near the blade and bone interface. These irrigation systems can be separate, requiring an additional device at the surgical site, or integrated. Although effective at flushing a surgical site of unwanted sources of added friction, these irrigation systems are relatively ineffective at actually cooling the blade at the blade and bone interface. For example, one design for a surgical saw that incorporates a means for irrigation comprises a channel between otherwise parallel portions of a saw blade through which fluid can flow out into the surgical site (See U.S. Pat. No. 5,087,261). This channel, though, can be easily compacted with surgical debris, rendering the integrated irrigation system unusable. In addition, providing a channel between parallel portions of the saw blade necessarily increases the likelihood of a wider, more uneven cut. Other designs for an oscillating bone saw include outlets along the blade's edge to facilitate irrigation along the blade and bone interface (See U.S. Pat. Nos. 4,008,720 and 5,122,142). However, these channels can be similarly compacted with surgical debris, rendering them useless. More so, channels along the very blade edge result in a blade edge that is not continuous, which reduces the cutting efficiency of the blade. Despite any potential efficacy in flushing a site of surgical debris, these systems do very little to actually cool the very blade edge, specifically at the blade and bone interface. Additionally, having copious amounts of irrigation fluid in the surgical site can hamper the surgeon's ability to visualize important anatomic structures.

Just as with saws used to cut wood, metal, and plastic, a user can avoid rough or uneven cuts by using a saw blade that incorporates more teeth along the edge of the blade and/or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut. Still, the improvement is not substantial enough to consider these measures a long-term solution with respect to producing smooth bone cuts. In fact, adding teeth or guiding the blade edge have little effect in preventing inadvertent tearing of neighboring soft tissues. Although efforts are taken to protect soft tissues from damage and prevent significant blood loss, the inherently close confines typical in performing any osteotomy make it extremely difficult to completely eliminate such damage, especially to those tissues that are unseen or positioned beneath the bone being cut. This is compounded by the fact that the saw blades used with many oscillating and reciprocating bone saws are relatively large.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the blade's edge by way of an ultrasonic horn. Being powered by sound waves, neighboring soft tissues are not damaged by these types of blades because the blade's edge effectively rebounds due to the elasticity of the soft tissue. Thus, the significant blood loss common with use of traditional bone saws is prevented. In addition, significantly more precise cuts are possible using ultrasonic bone cutting devices, in part, because the blade's edge does not require serrations. Instead, a continuous and sharpened edge, similar to that of a typical scalpel, enables a user to better manipulate the surgical device without the deflection caused by serrations, which is common when using oscillating and reciprocating bone saws. Although ultrasonic cutting blades are advantageous in that they are less likely to tear neighboring soft tissues and more likely to produce relatively more even cuts, these types of blades still generate considerable amounts of heat.

As with traditional bone saws, separate or integrated irrigation systems are often utilized in order to flush the surgical site and generally provide some measure of cooling effect to the blade. However, many of these blades suffer from the same disadvantages as traditional bone saws that have tried to incorporate similar measures. For example, providing openings along the blade's edge through which fluid flows introduces voids in the cutting edge, thereby inhibiting the cutting efficiency of the blade (See U.S. Pat. No. 5,188,102). In addition, these fluid openings can be readily compacted with surgical debris, rendering them useless for their intended function. In other blade designs, the continuity of the blade is maintained and a fluid outlet is positioned just before the blade's edge (See U.S. Pat. No. 8,348,880). However, this fluid outlet merely irrigates the surgical site since it is positioned too far from the blade and bone interface to actually provide the necessary cooling effect. Also, it irrigates only one side of the blade. Another design for an ultrasonic cutting device, which claims to cool the blade, incorporates an irrigation output located centrally along the longitudinal axis of the blade (See U.S. Pat. No. 6,379,371). A recess in the center of the blade tip allows fluid to flow out of this output and toward the blade's edge, flow that is propelled by a source of pressure. However, the positioning of this irrigation output within the contour of the blade tip results in a bifurcation or splitting of the irrigation flow, such splitting tending to distribute fluid at an angle away from the blade's edge. Mentioned above, the excessive heat generated using any cutting blade, including an ultrasonic cutting blade, is focused most significantly at the blade and bone interface. This example for an ultrasonic blade with cooling capabilities, then, does little to actually cool the blade at the blade and bone interface, but instead serves merely to flush debris from the surgical site. Again, having copious amounts of irrigation fluid in the surgical site can hamper the surgeon's ability to visualize important anatomic structures. Furthermore, this ultrasonic blade is not well-suited to cutting large cross-sections of bone and is used almost exclusively in spine, oral or maxillofacial surgeries, which involve cutting of small bones.

Even assuming that any of the irrigation systems incorporated into the various bone saws provide some measure of cooling, thermal burning of both neighboring soft tissues and bone surfaces remains a significant problem. Because the working surface of the blade also moves rapidly, considerable heat is generated along its length, too. The dynamic motion of the surface of the blade contacts neighboring soft tissues, potentially burning them. With respect to an osteotomy, as the blade passes through the cross-section of bone, the freshly-cut bone surfaces remain in constant and direct contact with the rapidly vibrating shaft of the blade. As a result, it is not uncommon to burn the bone, produce smoke and, more importantly, kill osteocytes. In fact, simply lengthening an ultrasonic blade to accommodate large cross-sections of bone tissue, for example, increases the surface area through which heat can transfer and, thus, is avoided by manufacturers of these types of blades. While irrigation directed specifically toward the blade's leading edge may provide some measure of cooling at the blade and bone interface, irrigation alone is insufficient in trying to avoid prolonged exposure of bone tissue, for example, to temperatures in excess of 47° C. Therefore, there remains a need for a surgical device that is capable of cutting bones with large cross-sections, such as the femur, while maintaining a working temperature along the entirety of the blade shaft that does not inhibit proper healing of the bone tissue.

For at least the aforementioned reasons, there is a need for improved surgical devices and techniques.

BRIEF DESCRIPTION OF THE DRAWINGS

Figure 1:
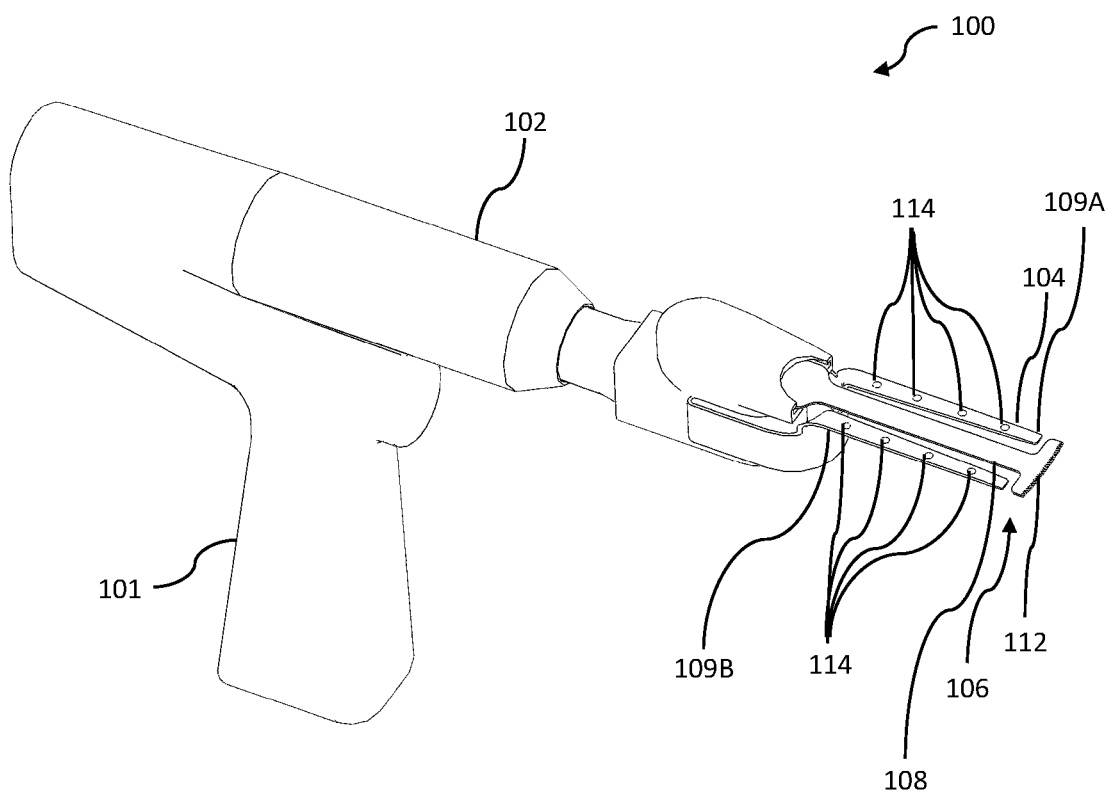
Figure 2:
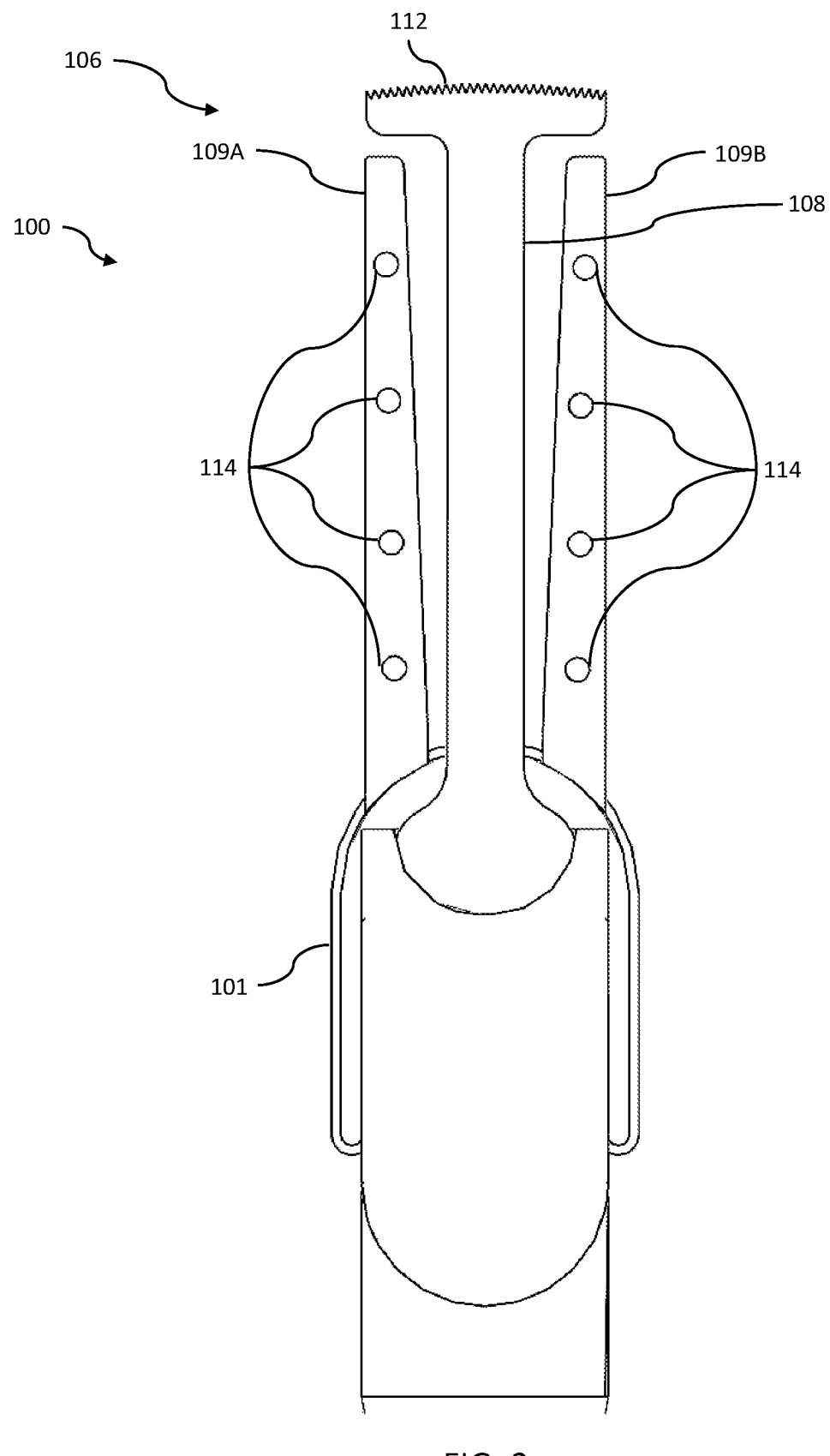
Figure 3:
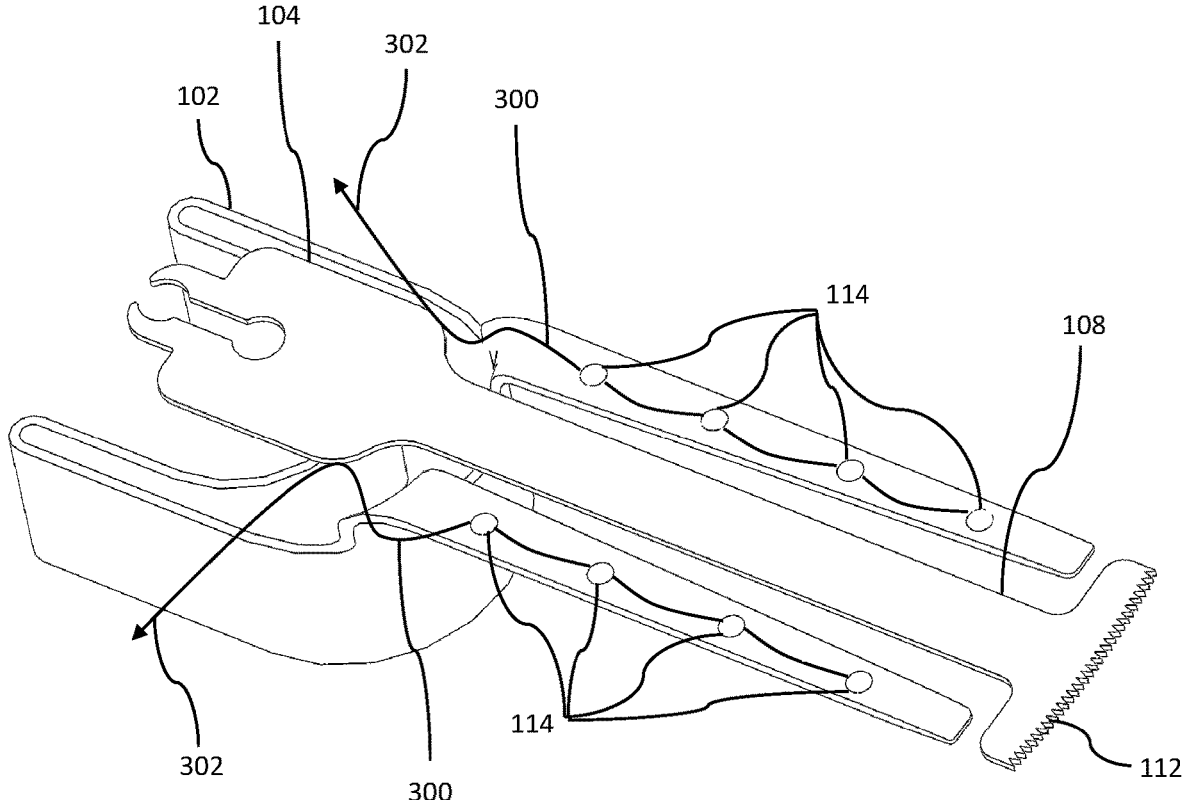
Figure 4:
Figure 5:
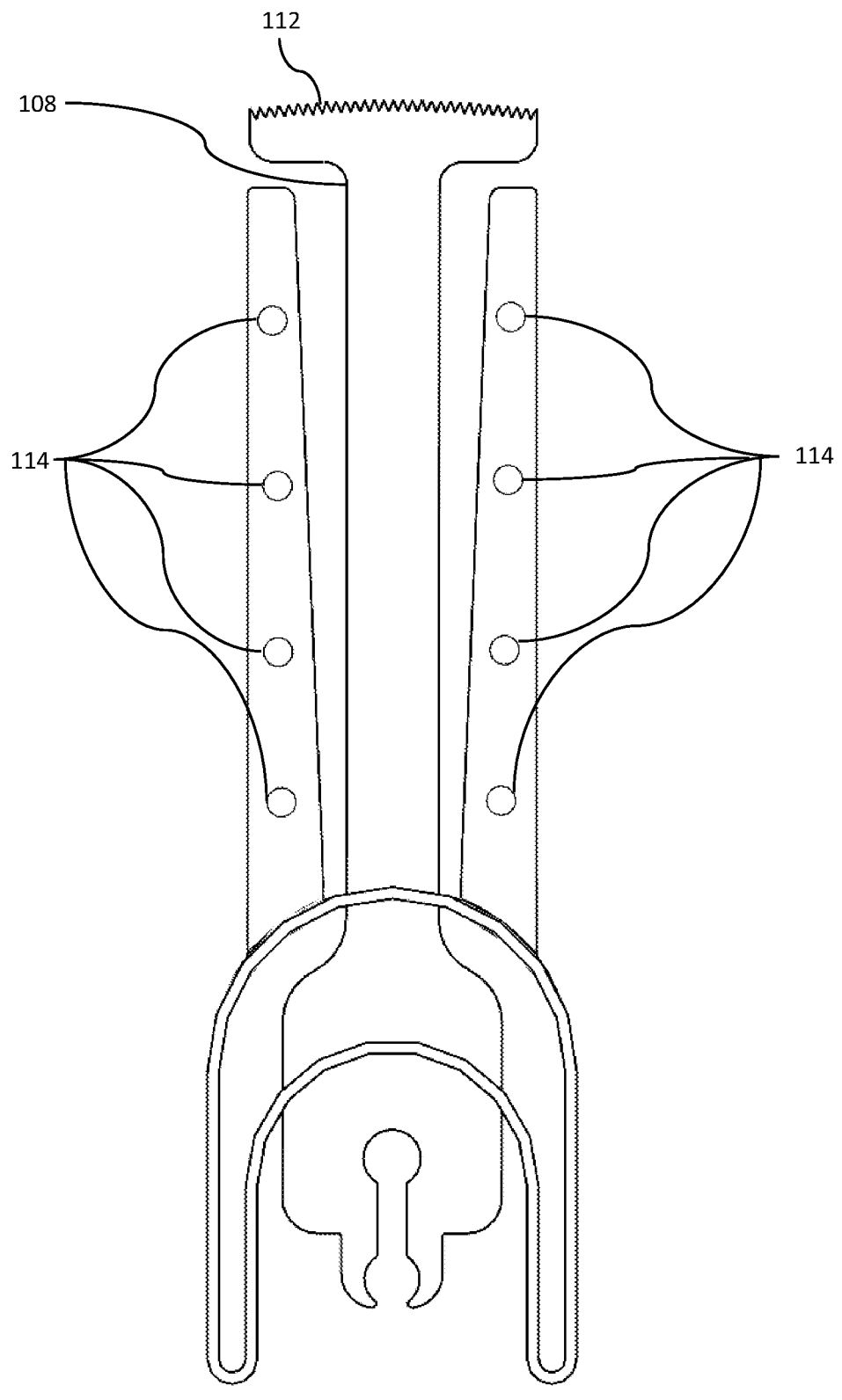
Figure 6:
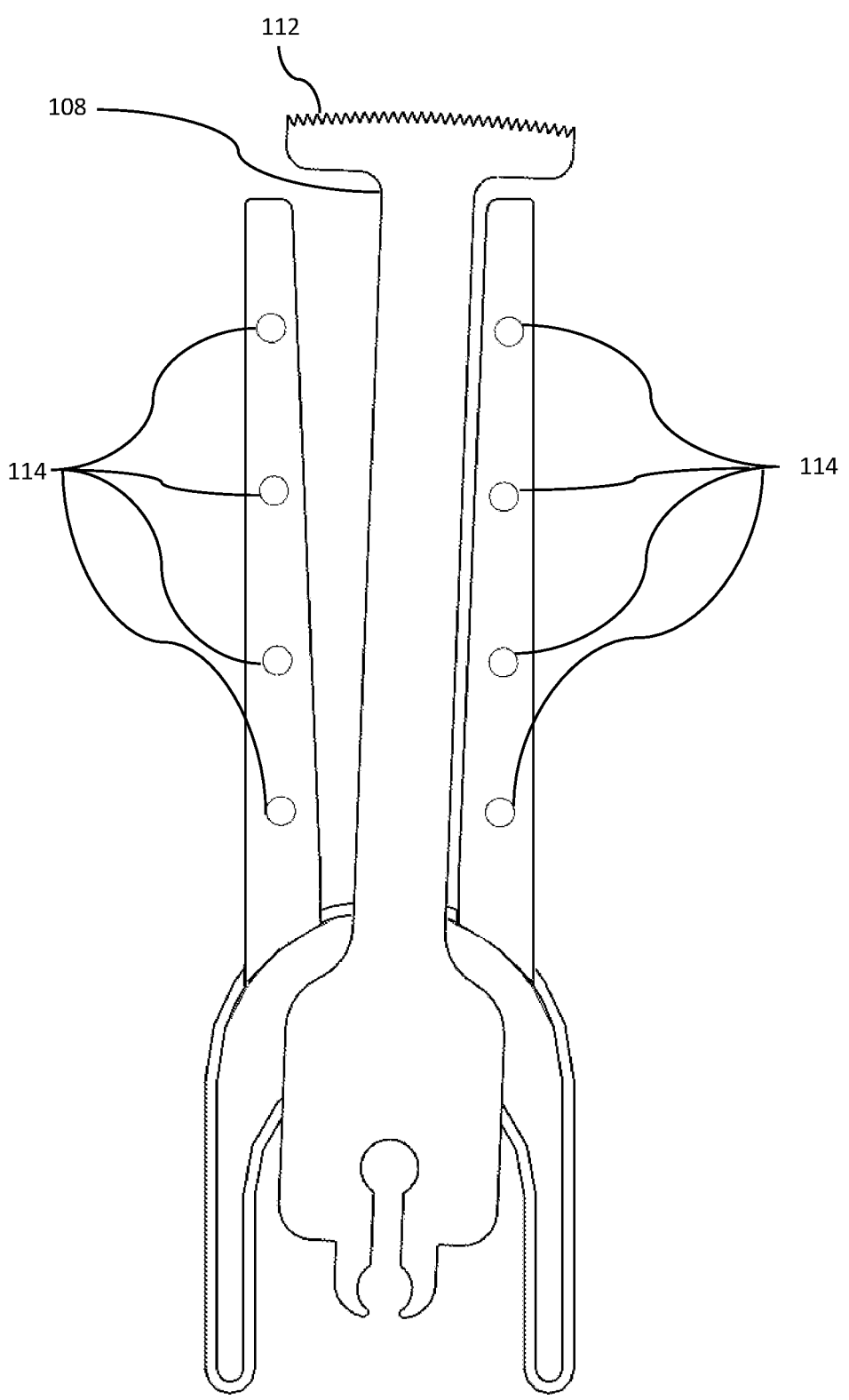
Figure 7:
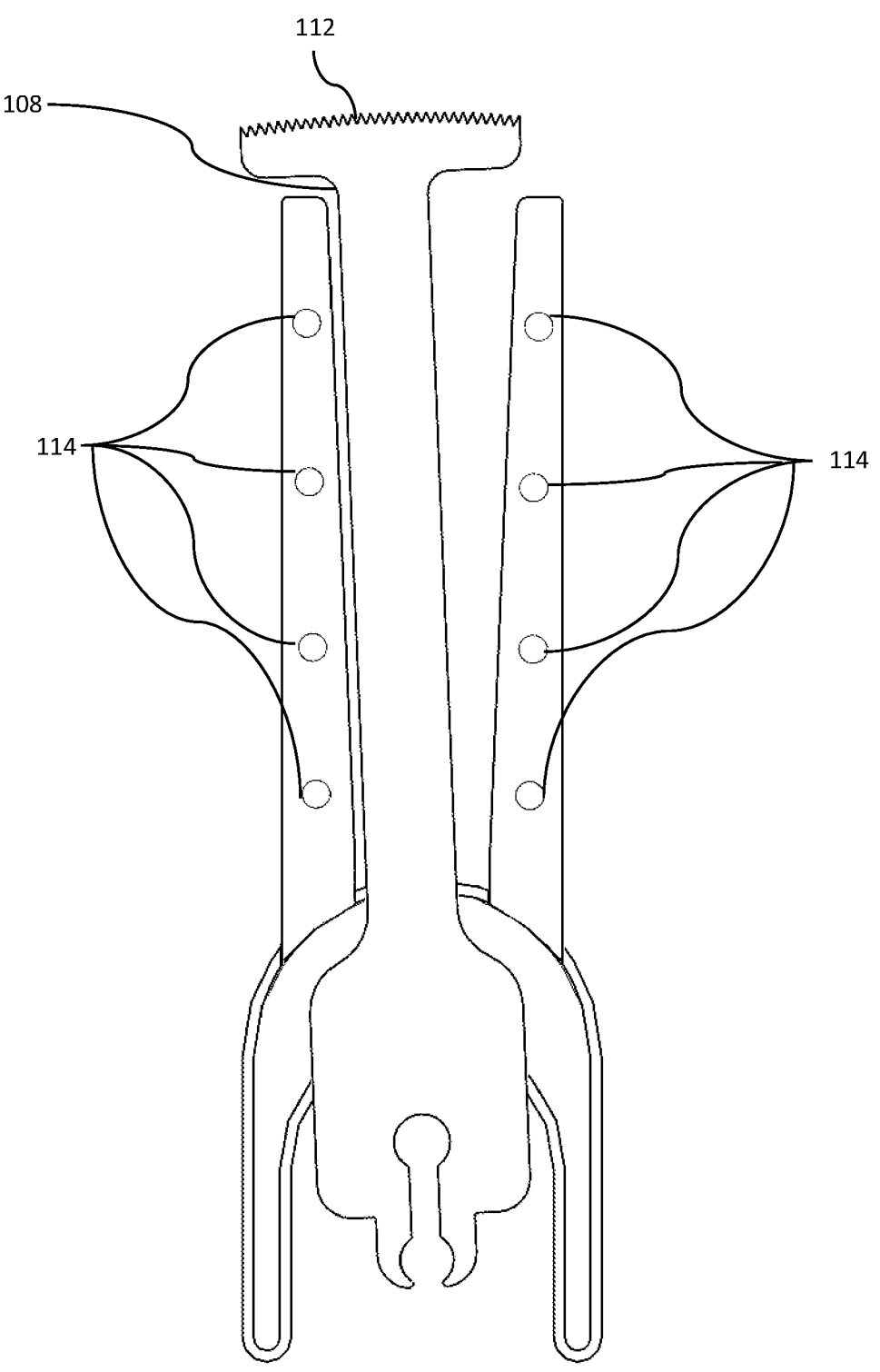
Figure 8:
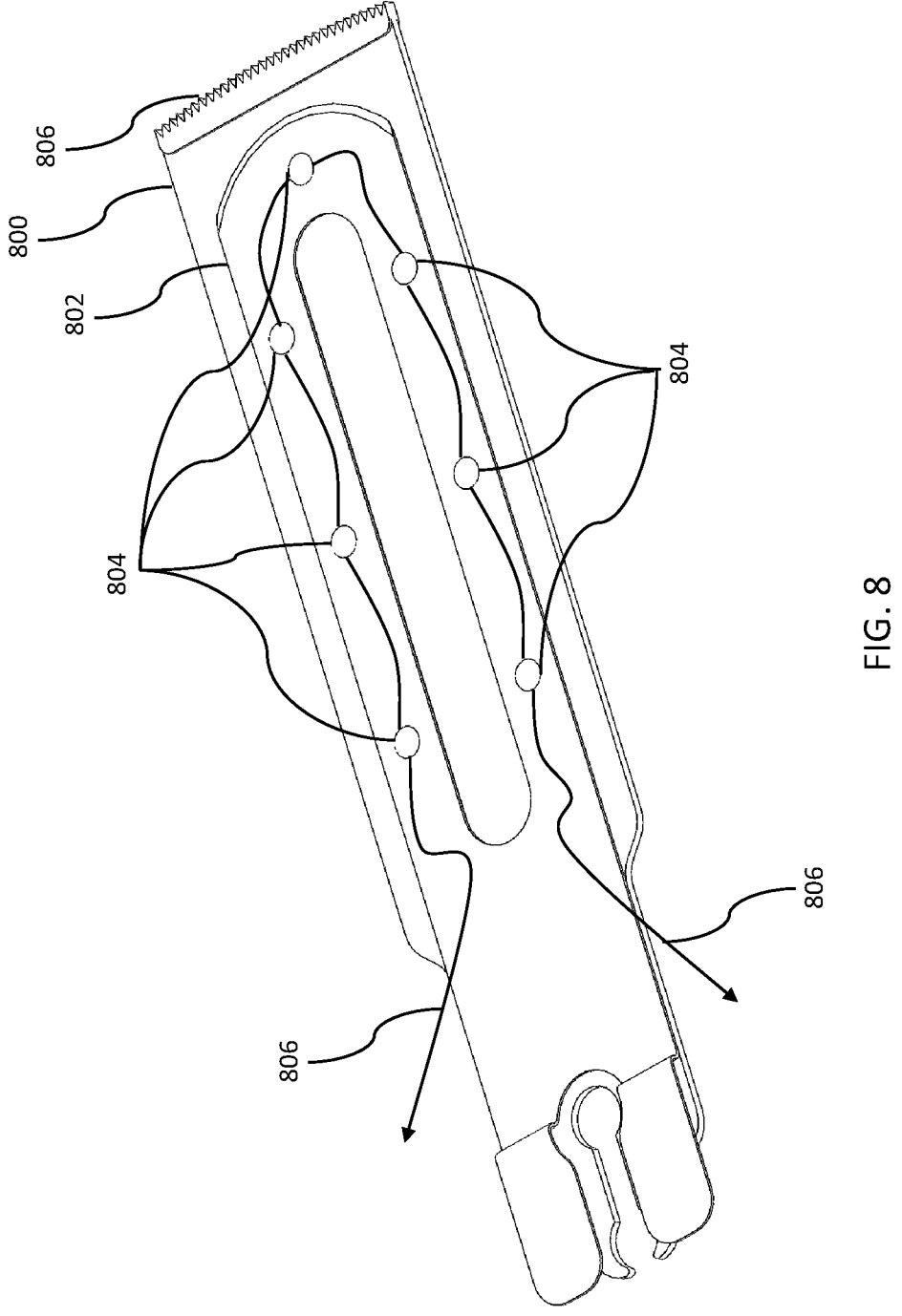
Figure 9:
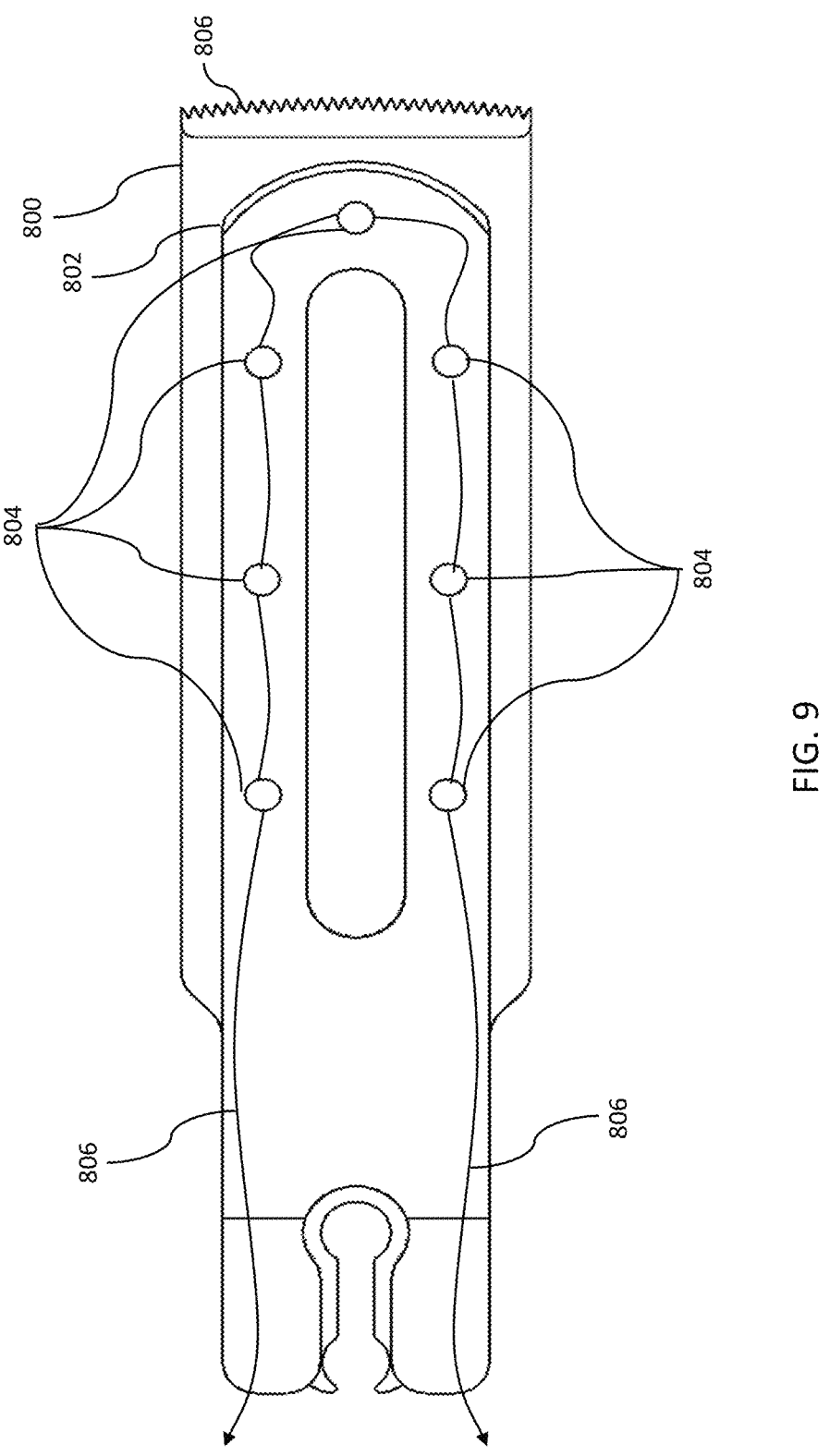
Figure 10:
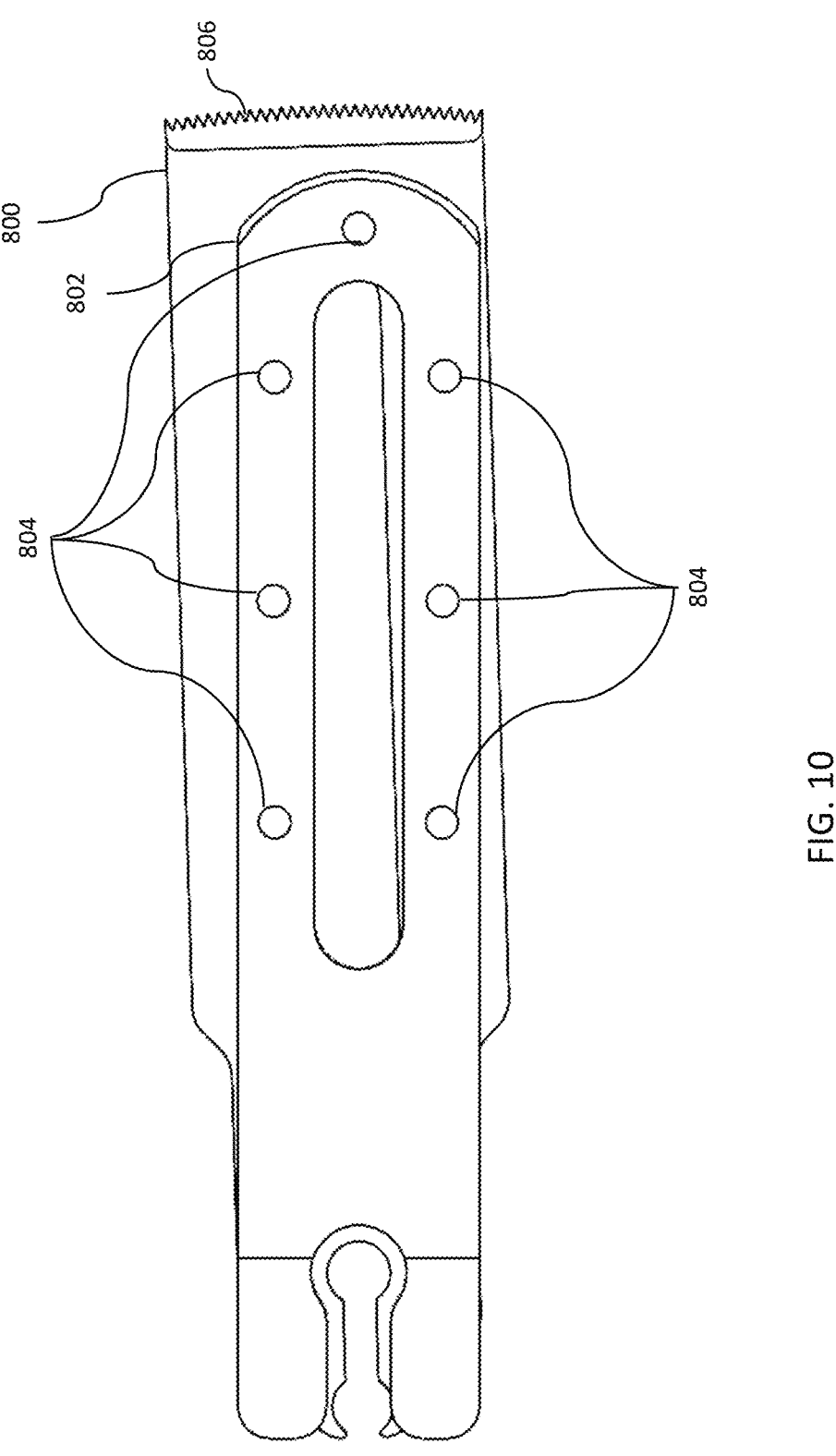
Figure 11:
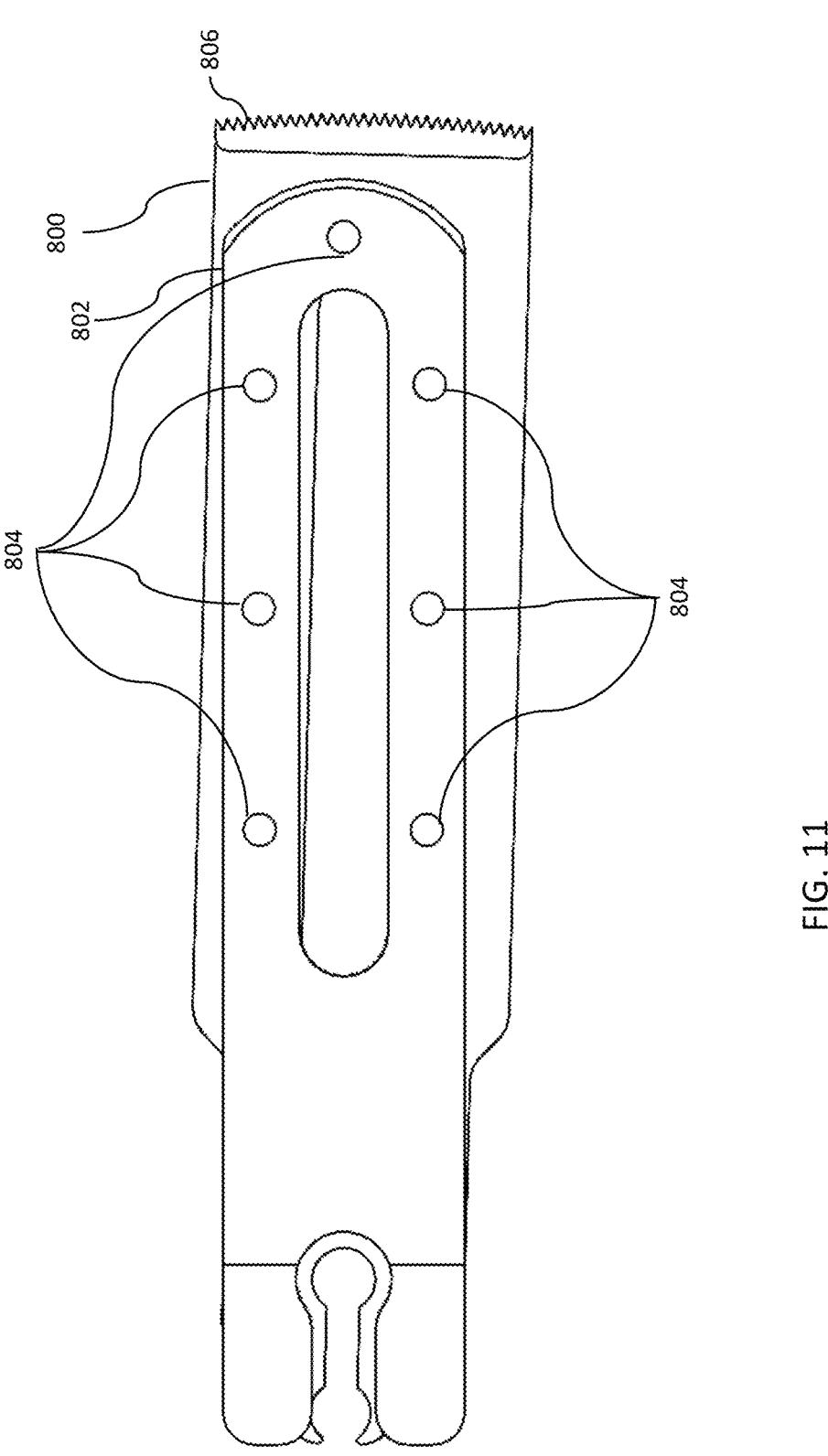
Figure 12:
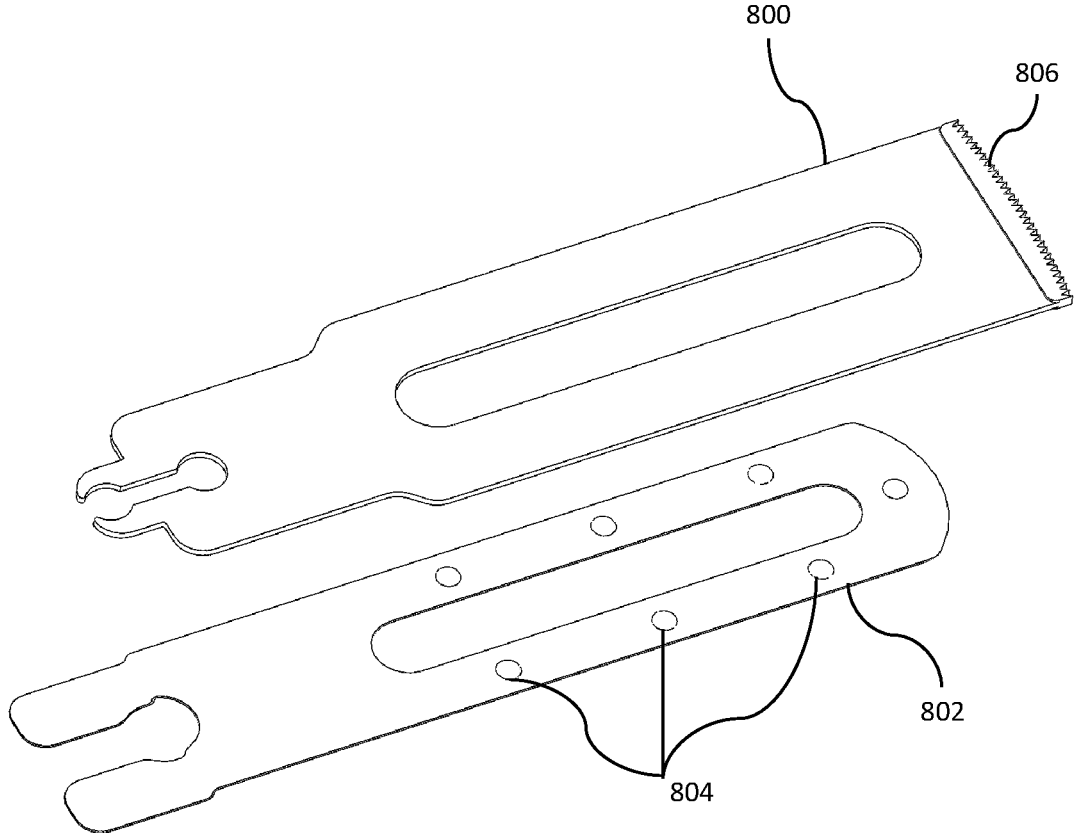
Figure 13:
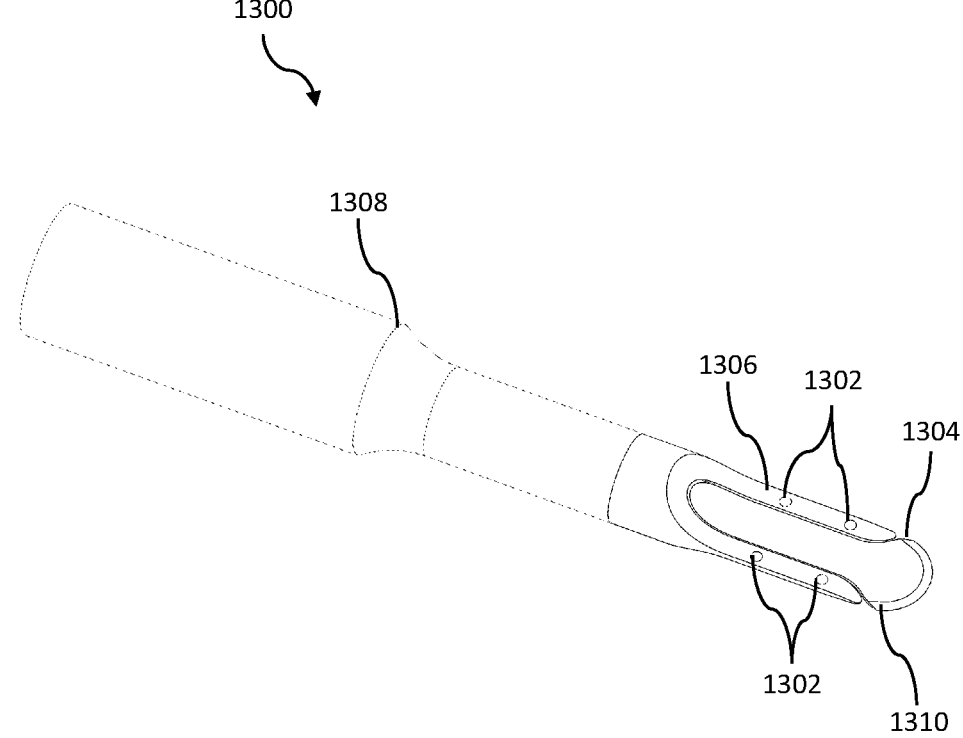
Figure 14:
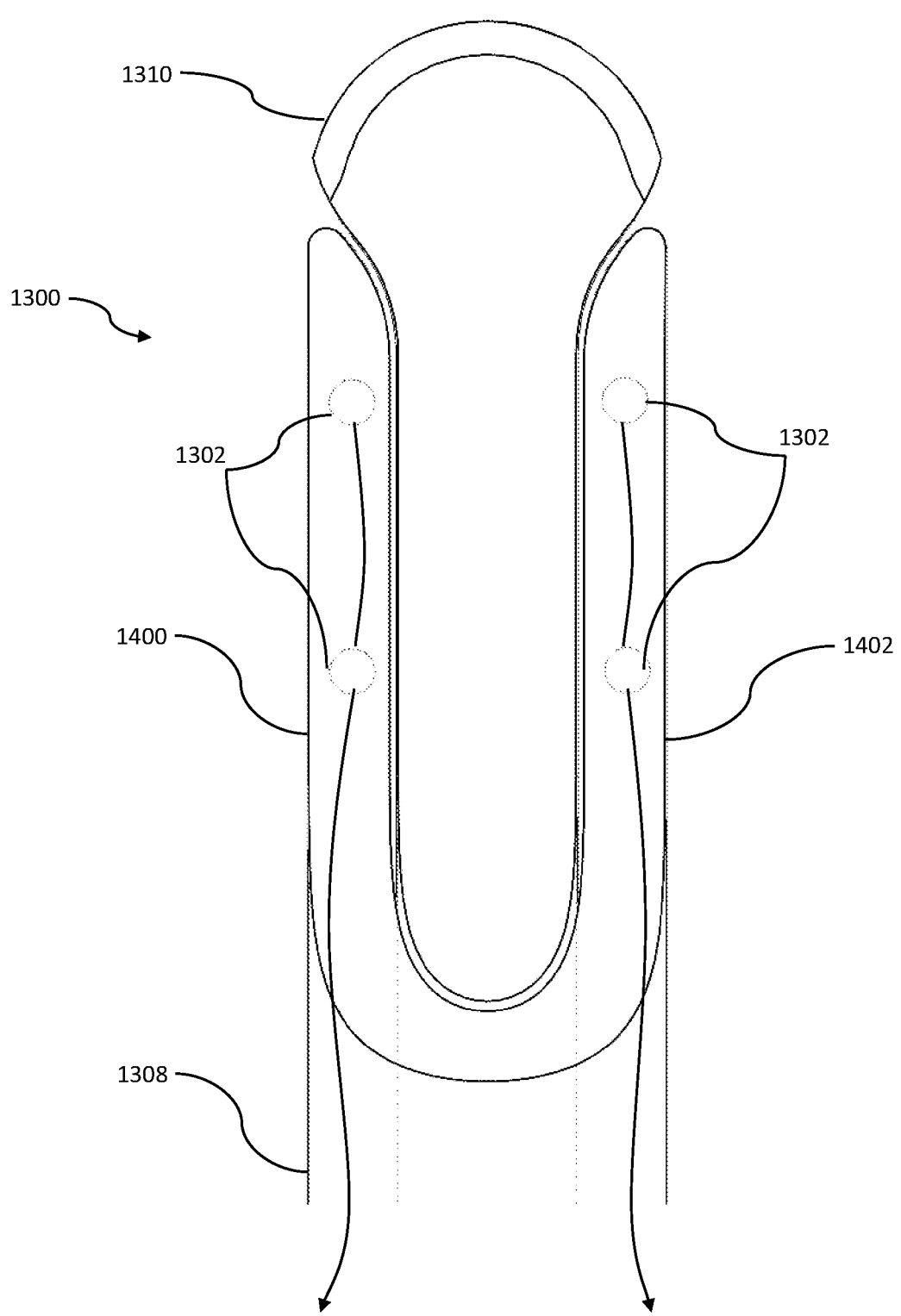
Figure 15:
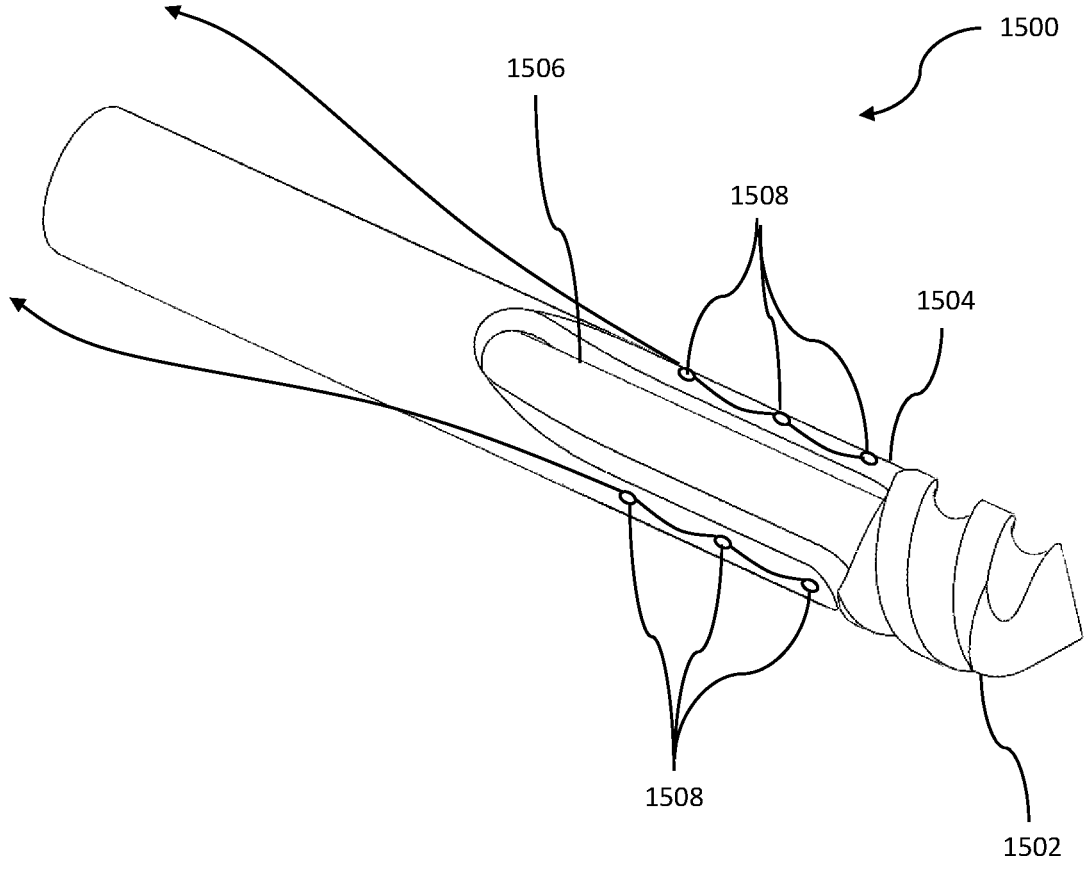
Figure 16:
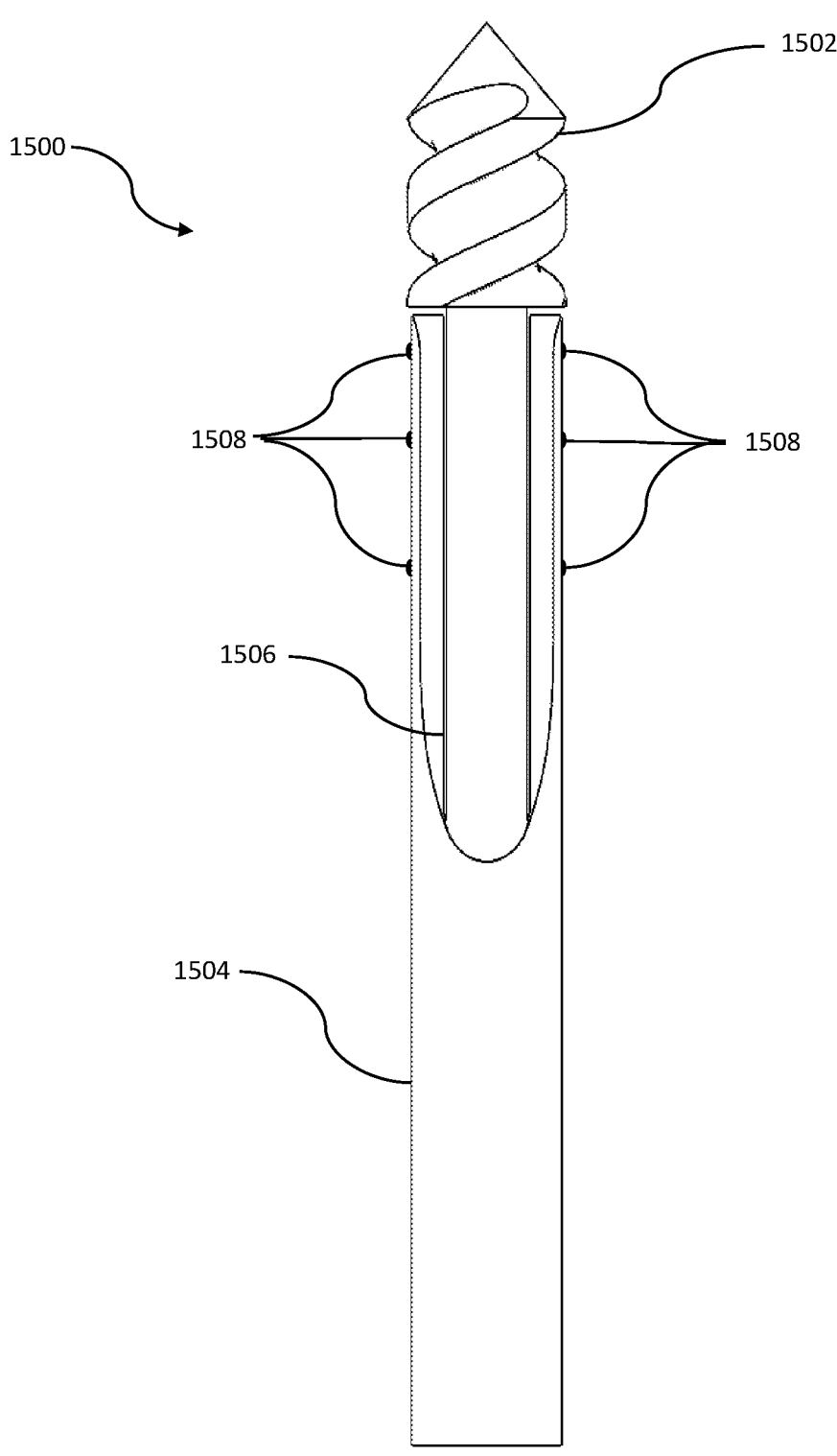
Figure 17:
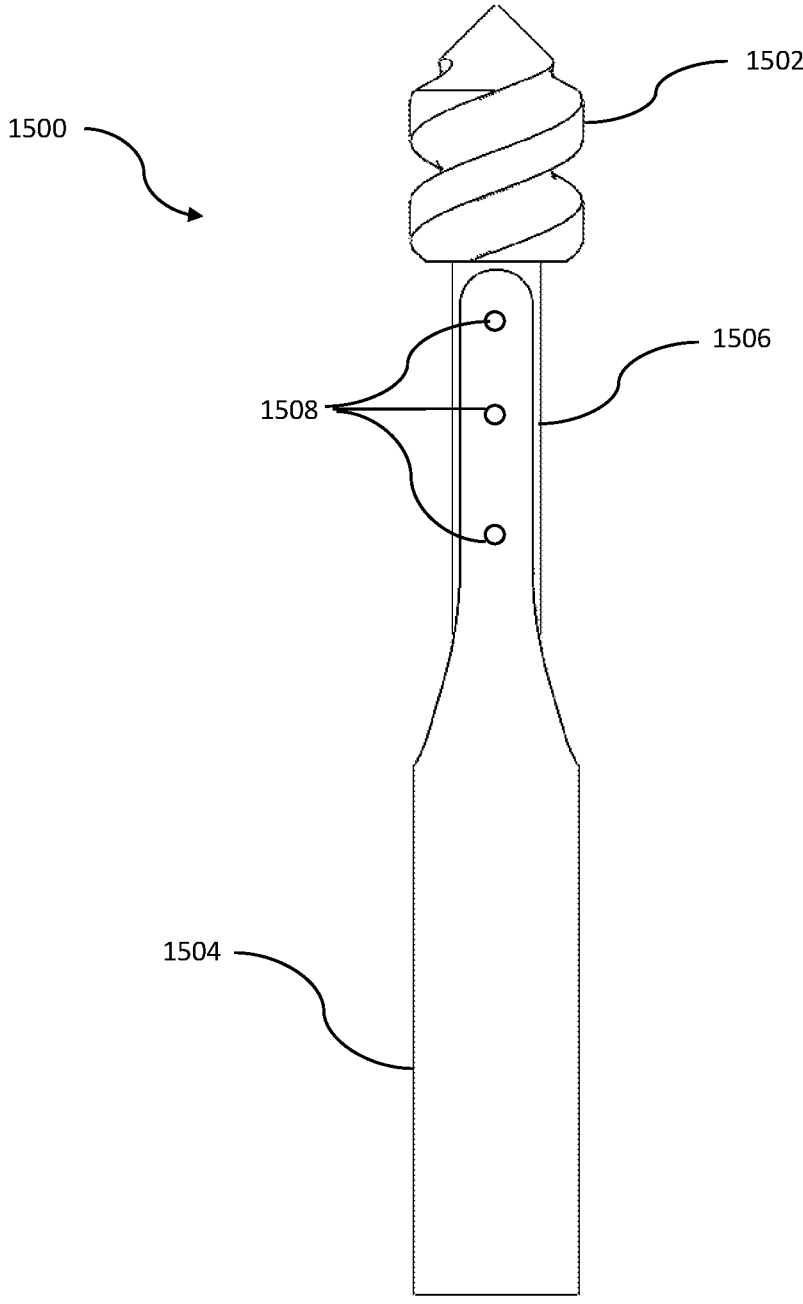

Having thus described the presently disclosed subject matter in general terms, reference will now be made to the accompanying Drawings, which are not necessarily drawn to scale, and wherein:

FIG. 1 is a top perspective view of a cutting device in accordance with embodiments of the present disclosure;

FIG. 2 is a top view of the cutting device shown in FIG. 1;

FIG. 3 is a top perspective view of the blade working body and the static casing of the cutting device shown in FIGS. 1 and 2;

FIG. 4 is a top view of the blade working body and the static casing of the cutting device with electrical wiring as shown in FIG. 3;

FIG. 5 is a bottom view of the blade working body and the static casing of the cutting device as shown in FIG. 3;

FIGS. 6 and 7 are top views of the blade working body of FIGS. 3-5 at a far right position and a far left position, respectively;

FIGS. 8 and 9 are a top perspective view and a top view, respectively, of another example of a blade working body and the static casing with in-situ temperature sensors in accordance with embodiments of the present disclosure;

FIGS. 10 and 11 are top views of the blade working body of FIGS. 8 and 9 at a far left position and a far right position, respectively;

FIG. 12 is an exploded, top perspective view of the blade working body and the static casing shown in FIGS. 8-11;

FIG. 13 is a top perspective view of an ultrasonic static rail, cutting device with temperature sensors in accordance with embodiments of the present disclosure;

FIG. 14 is a top view of the ultrasonic static rail, cutting device shown in FIG. 11;

FIG. 15 is a top perspective view of a cutting device having a drill portion with temperature sensors in accordance with embodiments of the present disclosure; and FIGS. 16 and 17 depict a top view and a side view, respectively, of the cutting device shown in FIG. 15.

SUMMARY

The presently disclosed subject matter medical cutting devices with static components having temperature sensors and related methods. According to an aspect, a static casing having a width of substantially a first distance. The cutting device also includes a working body having a first end and a second end. The first end is configured to operatively connect to a source of movement. The second end includes a cutting component. The working body has a width of substantially a second distance. The second distance is greater than the first distance.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As referred to herein, the term "cutting device" can be any suitable component movable for cutting into or generally transforming a material (e.g., bone). The cutting device can include a blade that operates through large or small (e.g., vibrations) mechanical motion. The motion can be in a specific direction(s). For example, the cutting device can be moved in an oscillating manner, flexing, bending, rotating, torsionally, longitudinally, and the like.

In some applications, there is a need to measure temperature in real time at the working surface of the blade. The present disclosure provides device that position temperature sensors in and around the cutting plane and bone-blade interface. This provides important temperature measurements in-situ on a cutting device. These measurements can be important, because they provide valuable feedback on when temperatures approach or reach the necrotic limit, thereby allowing an action to be performed to prevent thermal necrosis of the surrounding bone. For example, if the necrotic limit is reached during an osteotomy, then the blade could be stopped or a cooling mechanism activated. This could be applicable to manually operated devices or in a robotic setting where feedback can be collected and applied based on the desired outcome. While one feasible application of the technology would be to leverage the technology to prevent thermal necrosis one can envision scenarios where ensuring higher temperatures are met (e.g., heating to prevent blood loss) or potentially leveraging temperature based data to understand differences in bone quality between patient populations, e.g. identifying differences in the rate at which certain types of bone absorb heat. In the context of reducing heat transfer to bone, protecting the viability of the bone is crucial to allow for bone in-growth/osteointegration (e.g., cementless implant applications, union of bone interfaces, etc.).

FIG. 1 illustrates a top perspective view of a cutting device 100 in accordance with embodiments of the present disclosure. Referring to FIG. 1, the device 100 includes a handle 101, a housing 102, and a static component 104. In this example, the static component 104 is a static casing. Although these components are not shown in FIG. 1, the housing 102 may contain in an interior space therein for components, such as any suitable transducer or motor, to produce a desired mechanical motion with a cutting end, generally designated 106. It is noted that in this example the device 100 is described as being an oscillating saw blade, but it may alternatively be of any other suitable type (e.g., such as an ultrasonic transducer driving the blade through piezoelectric elements and smaller vibrations). The oscillating motor, which may be suitably powered to produce motion through the working surface of the blade to its blade edge, can be operatively attached to an end of a blade working body 108 that is closest to the housing 102. Oscillatory motion produced by the transducer/motor can propagate along a main body of the blade working body 108 towards an end of the blade working body 108 that opposes the end of the blade working body 108 that is attached to the oscillatory transducer/motor. It is noted that any other suitable motion may be produced alternative to mechanical oscillations such as those produced by traditional bone saws (e.g., such as those produced by ultrasonic cutting devices that use smaller scale vibrations).

The static casing 104 can sheath and support the upper and lower portion of the blade working body 108. In the particular example, the static casing 104 includes portions 109A and 109B that are positioned on opposing sides of the blade working body 108 as depicted. The static casing 104 and the blade working body 108 can be spaced from each other by an air gap or otherwise be in direct contact to support the blade throughout the cutting process. The static casing 104 can be stationary or at least substantially stationary with respect to a source of movement. The air gap can reduce transfer of energy from the blade working body 108 and, thus, heat to the static casing 104. It is noted that the casing 104 may be made of any suitable insulative material, such as ceramic/polymer or any other suitable medical grade material, for preventing or minimizing heat transfer to the bone. Air can be present around the casing and/or blade.

A cutting end 106 can be a blade tip configured to cut, ablate, abrade or otherwise transform, for example, bone or other tissue. The cutting end 106 includes a top surface 110 and an opposing bottom surface. The cutting end 106 defines at least one blade edge 112. In this example, the blade edge 112 has serrations for cutting, ablating, abrading, or otherwise transforming bone or other tissue. In the alternative, the blade edge 112 is a continuous, planar arc, and sharpened along its entirety for cutting, ablating, abrading, or otherwise transforming bone or other tissue.

With continuing reference to FIG. 1, portions 109A and 109B of the static casing 104 include in-situ temperature sensors 114. The temperature sensors 114 are configured to detect (or sense) actual temperature and/or temperature fluctuations at their respective locations. The temperature sensors 114 can be positioned for detecting temperature level(s) of a work space near the blade working body 108. The temperature sensors 114 can be attached to portions 109A and 109B and/or any other embodiment that decouples the motion of the bone from the blade (e.g., static inserts, static rails, static casings, etc.). By positioning on the portions 109A and 109B, motion of the temperature sensors 114 can be limited to reduce the likelihood of damage. Since the static casing 104 does not move relative to the motion of the blade working body 108, they measure temperature based on location within the cutting plane and not based on the rapid/dynamic motion of the blade working body 108 itself. These ensure results are not biased and locationally remain more consistent relative to their position on the blade. Temperature sensors 114 can be operably connected via lines or traces to electronic circuitry (not shown) configured to receive electrical signals indicative of the detected temperatures and/or temperature fluctuations.

The electronic circuitry connected to the temperature sensors 114 can be used to monitor the cutting temperature in real-time for preventing bone necrosis. The electronic circuitry can be used to provide feedback to stop cutting of a threshold temperature level is reached. The feedback and reach of the threshold temperature level can be determined based on electrical signals received from the temperature sensors 114. Further, the electronic circuitry can be configured to sense varying bone types and to indicate breaching through a layer. (i.e., if temperature drops on a given sensor it may indicate lack of contact with bone). The electronic circuitry may interface with any number of software, hardware, and/or firmware (e.g., to cut the motor out or provide haptic feedback to inform an operator that a certain threshold is reached), or externally display with a display or LED for notifying the operator that a certain threshold is reached.

FIG. 2 illustrates a top view of the cutting device 100 shown in FIG. 1. Referring to FIG. 2, it can be seen that portions 109A and 109B are spaced apart from the static casing 108 as they are closer to blade edge 112. This provides for spacing for leftward and rightward movement of the blade edge.

FIG. 3 illustrates a top perspective view of the blade working body 108 and the static casing 104 of the cutting device 100 shown in FIGS. 1 and 2. Referring to FIG. 3, electrical wiring 300 for connecting temperature sensors 114 are shown. Ends 302 of the electrical wiring 302 can operatively connect to electronic circuitry for receiving temperature readings of the temperature sensors 114 as described herein. FIG. 4 illustrates a top view of the blade working body 108 and the static casing 104 of the cutting device 100 with electrical wiring 300 as shown in FIG. 3. FIG. 5 illustrates a bottom view of the blade working body 108 and the static casing 104 of the cutting device 100 as shown in FIG. 3.

It is noted that FIGS. 3-5 depict the blade working body 108 at a neutral position, or a position approximately at a middle of its full range of motion. Particularly, the blade working body 108 can move rightward and leftward, and FIGS. 3-5 show the blade working body 108 at an approximately mid-way position between the farthest left position and the farthest right position. FIGS. 6 and 7 illustrate top views of the blade working body 109 of FIGS. 3-5 at a far right position and a far left position, respectively.

FIGS. 8 and 9 illustrate a top perspective view and a top view, respectively, of another example of a blade working body 800 and the static casing 802 with in-situ temperature sensors 804 in accordance with embodiments of the present disclosure. The blade working body 800 and the static casing 802 may be operably attached to other components of a cutting device, such as the handle 101, housing 102, and source of movement, as described in the embodiment of FIG. 1 or other such components for cutting material.

Referring to FIGS. 8 and 9, the temperature sensors 804 are configured to sense actual temperature and/or temperature fluctuations at their respective locations. The temperature sensors 804 can each be attached to the static casing 802 and/or any other embodiment that decouples the motion of the bone from the blade (e.g., static inserts, static rails, static casings, etc.). By position on the static casing 802, motion of the temperature sensors 804 can be limited to reduce the likelihood of damage. Since the casing does not move relative to the motion of the blade, they measure temperature based on location within the cutting plane and not based on the rapid/dynamic motion of the cutting device itself. These ensure results are not biased and locationally remain more consistent relative to their position on the blade. The blade working body 800 is positioned below the temperature sensors 804 and the static casing 802. The temperature sensors 804 can be operably connected via lines 806 to electronic circuitry (not shown) configured to receive electrical signals indicative of the detected temperatures and/or temperature fluctuations. The blade working body 800 includes a blade edge 808.

The electronic circuitry connected to the temperature sensors 804 can be used to monitor the cutting temperature in real-time for preventing bone necrosis. The electronic circuitry can be used to provide feedback to stop cutting of a threshold temperature level is reached. Further, the electronic circuitry can be used to sense varying bone types and to indicate breaching through a layer (i.e. if temperature drops on a given sensor it may indicate lack of contact with bone). The electronic circuitry could interface with any number of software (e.g. to cut the motor out or provide haptic feedback to tell the user that a certain threshold is reached) or external displays like a screen or LEDs that notify the user that a certain threshold is reached.

It is noted that FIGS. 8 and 9 depict the blade working body 800 at a neutral position, or a position approximately at a middle of its full range of motion. Particularly, the blade working body 800 can move rightward and leftward, and FIGS. 8 and 9 show the blade working body 800 at an approximately mid-way position between the farthest left position and the farthest right position. FIGS. 10 and 11 illustrate top views of the blade working body 800 of FIGS. 8 and 9 at a far left position and a far right position, respectively.

FIG. 12 illustrates an exploded, top perspective view of the blade working body 800 and the static casing 802 shown in FIGS. 8-11.

FIG. 13 illustrates a top perspective view of an ultrasonic static rail, cutting device 1300 with temperature sensors 1302 in accordance with embodiments of the present disclosure. Referring to FIG. 13, a blade working body 1304, a static casing 1306, and a housing 1308 may be operably attached to other components of the cutting device 1300, such as the handle 101 and source of movement as described in the embodiment of FIG. 1 or other such components for cutting material. The blade working body 1304 can include a curved blade edge 1310 that is operatively connected to a source of movement for rapid oscillation forward and backward.

FIG. 14 illustrates a top view of the ultrasonic static rail, cutting device 1300 shown in FIG. 11. Referring to FIG. 14, the blade edge 1310 is on an end of the blade working body that extends farther than the static casing 1306. It is noted that during operation for cutting or transforming material, such as bone, only rails 1400 and 1402 of the static casing 1306 contact the material (e.g., bone) when in the cutting plane. Lines 1404 are operatively connected to the temperature sensors 1302 in accordance with embodiments of the present disclosure.

FIG. 15 illustrates a top perspective view of a cutting device 1500 having a drill portion 1502 with temperature sensors 1504 in accordance with embodiments of the present disclosure. Referring to FIG. 15, the drill portion 1502 may be operatively connected to a source of movement for rapidly rotating the drill portion 1502 for drilling into or otherwise transforming a material, such as bone. The drill portion 1502 can be supported by a body 1504. Particularly, a rotatable shaft 1506 attached to the drill portion 1502 may be surrounded and held by the body 1504. The body 1504 may be considered a static casing.

With continuing reference to FIG. 15, the cutting device 1500 may include temperature sensors 1506 for detecting temperature in accordance with embodiments of the present disclosure. The temperature sensors 1506 are aligned along the body 1504. Alternatively, the temperature sensors may be any suitable number and in any suitable arrangement. FIGS. 16 and 17 illustrate a top view and a side view, respectively, of the cutting device 1500 shown in FIG. 15.

It is noted that embodiments of the present disclosure are described as producing or having oscillatory saw blade movement or any other suitable source for motion. It is noted that in the alternative the movement may be any suitable type of movement produced by any suitable source (e.g., such as an ultrasonic transducer driving the blade through piezoelectric elements and smaller vibrations). Further, cutting may be applied to any suitable material or technical field. Suitable mechanical sources could include anything from piezoceramics, electro-mechanical motors, user generated hand motion, etc. However, its important to note that all types of mechanisms can produce equivalent types of movements. These could include, but are not limited to, axial motion, bending motion, torsional motion, flexural motion, etc. It is also feasible that the source of mechanical motion can combine all of these modes of motion to create more complex movements. Regardless of the motion and/or the manner in which it is produced, there would be a resultant motion at the end of the functional device/blade edge. This motion would, under the claims of this patent, be captured within the bounds of the static casing which function to share load, decouple motion, and prevent heat transfer to the functional working surfaces. Examples include oscillating/sagittal/reciprocating medical bone cutting saws, medical rotary drills, medical rotary burs, construction hammer drills, construction rotary hammer, wood cutting axes, construction oscillating multi-tools, oscillating medical cast saws, cutting saws, etc. The principles of the claims presented in this patent could be applied to all of these devices with equivalently realized benefits.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:

1. A cutting device comprising:
an oscillating saw blade being configured for oscillation within a space by operable connection to a source of movement;
a static component being configured for operable connection to the source of movement, wherein the static component includes a first portion and a second portion that extends alongside of the saw blade and that defines the space; and
at least one first temperature sensor and at least one second temperature sensor attached to the first portion and the second portion, respectively, of the static component on opposite sides of the saw blade, wherein the at least one first temperature sensor and the at least one second temperature sensor are configured to detect a temperature level of a work space near the working body for monitoring a temperature of an object.

2. The cutting device of claim 1, wherein the oscillating saw blade comprises a blade edge.

3. The cutting device of claim 1, wherein the oscillating saw blade includes a first end and a second end, wherein the first end of the oscillating saw blade is operatively connected to the source of movement, and the second end of the working body extends beyond the static component.

4. The cutting device of claim 1, wherein the at least one first temperature sensor comprises a plurality of first temperature sensors, and wherein the at least one second temperature sensor comprises a plurality of second temperature sensors that are spaced apart along the first portion and the second portion, respectively of the static component.

5. The cutting device of claim 1, wherein the at least one first temperature sensor comprises further comprising a plurality of first temperature sensors, and wherein the at least one second temperature sensor comprises a plurality of second temperature sensors,
wherein the plurality of first temperature sensors are attached to the first portion, and
wherein the plurality of second temperature sensors are attached to the second portion.

6. The cutting device of claim 1, wherein the static component includes a first end and a second end, wherein the first end of the static component is attached to the source of movement and substantially stationary with respect to the source of movement.

7. The cutting device of claim 1, wherein the at least one first temperature sensor and the at least one second temperature sensor are operatively connected to electronic circuitry configured to detect a temperature level and provide feedback based on signals received from the at least one first temperature sensor and the at least one second temperature sensor.

8. The cutting device of claim 1, wherein the saw blade and the static component are substantially flat.

9. The cutting device of claim 8, wherein the saw blade and the static component are substantially within the same plane.

* * * * *